(12) United States Patent
Merlen et al.

(10) Patent No.: US 6,514,479 B1
(45) Date of Patent: Feb. 4, 2003

(54) EUO ZEOLITE COMPRISING CRYSTALS AND AGGREGATES OF CRYSTALS WITH SPECIFIC GRANULOMETRYS AND ITS USE AS A CATALYST IN THE ISOMERISATION OF C8 AROMATIC COMPOUNDS

(75) Inventors: Elisabeth Merlen, Rueil-Malmaison (FR); Fabio Alario, Neuilly sur Seine (FR); Olivia Martin, Nanterre (FR); Nathalie Ferrer, Montesson (FR); Sylvie Lacombe, Rueil-Malmaison (FR); Loïc Rouleau, Oullins (FR); Julia Magne-Drisch, Vilette de Vienne (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/471,323

(22) Filed: Dec. 23, 1999

(30) Foreign Application Priority Data

Dec. 23, 1998 (FR) .............................. 98 16421

(51) Int. Cl.⁷ ..................... C01B 39/04; B01J 29/06; B01J 29/064; C07C 5/22
(52) U.S. Cl. ................. 423/705; 423/709; 423/716; 423/717; 423/708; 502/60; 502/66; 502/73; 502/74; 585/481
(58) Field of Search ................. 423/705, 708, 423/709, 716, 717; 502/66, 73, 74, 60; 585/481

(56) References Cited

U.S. PATENT DOCUMENTS

| | | | |
|---|---|---|---|
| 3,323,876 A | * | 6/1967 | Arey, Jr. et al. |
| 4,593,138 A | * | 6/1986 | Casci et al. |
| 4,606,901 A | * | 8/1986 | Chu et al. |
| 4,640,829 A | * | 2/1987 | Rubin |

FOREIGN PATENT DOCUMENTS

| | | |
|---|---|---|
| EP | 0 042 226 | 12/1981 |
| EP | 0 159 845 | 10/1985 |
| WO | 98/16469 | 4/1998 |

OTHER PUBLICATIONS

XP–002108595—Crystallization of EU–1 and EU–2 in alkali and alkali–free systems, Glenn W. Dodwell et al., vol. 5, No. 3, (May 3, 1985), pp. 153–157.

* cited by examiner

Primary Examiner—David Sample
(74) Attorney, Agent, or Firm—Millen, White, Zelano & Branigan, P.C.

(57) ABSTRACT

The invention concerns a zeolite with structure type EUO comprising EUO zeolite crystals with a size of less than 5 $\mu$m, at least a portion of the EUO zeolite crystals being in the form of EUO zeolite aggregates, characterized in that the granulometry of the aggregates is such that Dv,90 is 500 $\mu$m or less. The invention also concerns the preparation of the zeolite and the use of the zeolite as a catalyst, for example in a process for isomerising aromatic compounds containing 8 carbon atoms per molecule.

58 Claims, No Drawings

EUO ZEOLITE COMPRISING CRYSTALS AND AGGREGATES OF CRYSTALS WITH SPECIFIC GRANULOMETRYS AND ITS USE AS A CATALYST IN THE ISOMERISATION OF C8 AROMATIC COMPOUNDS

TECHNICAL FIELD

The present invention relates to a zeolite with structure type EUO, characterized in that it is in the form of aggregates of zeolite crystals with a specific granulometry. The invention also relates to the use of the zeolite as a catalyst, more particularly as a catalyst for isomerising aromatic compounds containing 8 carbon atoms also known as "C8 aromatic cuts".

Zeolites with structure type EUO include EU-1, TPZ-3 and ZSM-50 zeolites. Such zeolites generally comprise at least one element X selected from silicon and germanium and at least one element T selected from the group formed by aluminium, iron, gallium, boron, titanium, vanadium, zirconium, molybdenum, arsenic, antimony, chromium and manganese, preferably aluminium, gallium, iron and boron, the overall atomic ratio X/T being 5 or more.

Isomerisation of ethylbenzene to xylenes or of a mixture of xylenes and ethylbenzene requires the presence of an acidic function and a group VIII metal. The main aim of isomerising C8 aromatic cuts is to produce para-xylene. Thus the discovery of novel catalysts which are active in converting a mixture of xylenes and ethylbenzene and which are selective, i.e., for which side reactions are minimised, is important. Such side reactions, which constitute substantial losses for the reaction, result from naphthene ring opening followed or otherwise by cracking or from dismutation and transalkylation reactions of C8 aromatics which lead to the formation of undesirable aromatic compounds.

PRIOR ART

United States patents U.S. Pat. No. 4,723,051 and U.S. Pat. No. 4,665,258 describe optimised formulations based on mordenite zeolites and a group VIII metal which result in catalysts with which side reactions remain non negligible.

French patent applications FR 97/16456 and FR 97/16458 describe a catalyst based on EUO zeolite characterized by good dispersion and good distribution of the group VIII metal and by good mechanical strength and its use in isomerising C8 aromatic compounds. That catalyst leads to a relatively good selectivity, but the activity, in particular for ethylbenzene conversion, is still to be improved.

EU-1 zeolite with structure type EUO, described in European patent EP-B1-0 42 226, has a unidimensional microporous framework, with a pore diameter of 4.1×5.7 Å (1 Å=1 Angström=$10^{-10}$ m) ("Atlas of Zeolite Structure Types", W. M. Meier and D. H. Olson, $4^{th}$ edition, 1996). Further, N. A. Briscoe et al. stated in their article in the review Zeolites (1988, 8, 74) that such unidimensional channels have lateral pockets with a depth of 8.1 Å and a diameter of 6.8×5.8 Å. The crystallite size, also termed EU-1 zeolite crystals, is in the range 1 to 3 microns and the aggregate size is in the range 425 to 1000 microns.

U.S. Pat. No. 4,640,829 concerns a ZSM-50 zeolite which according to the "Atlas of Zeolite Structure Types", W. M. Meier and D. H. Olson, $4^{th}$ Edition, 1996, has the same EUO structure type as EU-1 zeolite. That patent describes a mode of synthesising ZSM-50 comprising mixing a source of alkali metal ions, dibenzyldimethylammonium ions, silicon oxide, water and aluminium oxide.

EP-A-0 051 318 relates to TPZ-3 zeolite which, according to the "Atlas of Zeolite Structure Types", W. M. Meier and D. H. Olson, $4^{th}$ edition, 1996, has the same EUO structure type as EU-1 zeolite. That patent describes the use of TPZ-3 zeolite as a catalyst, for example for isomerising C8 aromatic compounds.

SUMMARY OF THE INVENTION

The present invention concerns a zeolite with structure type EUO comprising EUO zeolite crystals with a size of less than 5 μm, at least a portion of the EUO zeolite crystals being in the form of EUO zeolite aggregates, characterized in that the granulometry of the aggregates is such that Dv,90 is less than or equal to 500 μm. More particularly, the invention concerns EU-1 zeolite with structure type EUO.

IMPORTANCE OF THE INVENTION

EUO zeolite, for example EU-1 zeolite as defined in the present invention, used as a catalyst in association with at least one binder, at least one metal selected from elements from group VIII of the periodic table, said metal preferably being deposited on the binder, has improved catalytic performances for hydrocarbon transformation in terms of activity, such as isomerisation of C8 aromatic cuts, i.e., of mixtures constituted by xylenes and possibly ethylbenzene.

DESCRIPTION

The crystals and crystal aggregates of the zeolite with structure type EUO of the invention must have specific characteristics in terms of size. The zeolite with structure type EUO of the invention can be EU-1 zeolite, TPZ-3 zeolite or ZSM-50 zeolite. The term "aggregate" as used in the present description means an ensemble formed by at least two crystals of zeolite having at least one contact point between them.

The aggregate size is determined by laser diffraction granulometry. This measurement is carried out on powdered zeolite suspended in water. After a first measurement, the suspension is subjected to ultrasounds for thirty seconds then another measurement is carried out. The ultrasound used is characterized by a power of 50 W and a frequency of 50 kHz. This procedure is repeated until the result no longer changes (to ±5%). The size distribution of the aggregates defined by volume is calculated form the light signals collected by the detectors and using Fraunhofer theory. Dv,X is defined as the diameter of the equivalent sphere such that X% by volume of the aggregates have a diameter less than said diameter, after ultrasound. These characteristics are obtained directly during zeolite synthesis and/or by any method which can reduce the aggregate size, such as post-synthesis grinding or appropriate milling before forming.

The zeolite with structure type EUO of the invention contains at least one element X selected from silicon and germanium and at least one element T selected from the group formed by aluminium, iron, gallium, boron, titanium, vanadium, zirconium, molybdenum, arsenic, antimony, chromium and manganese, preferably aluminium, gallium, iron and boron, the overall atomic ratio X/T being 5 or more. The zeolite is characterized in that the zeolite crystal size must be less than 5 μm, preferably less than 0.5 μm and more preferably less than 0.2 μm, limits included, at least a part of the zeolite crystals being arranged in the form of aggregates, said crystal aggregates having a granulometry such that the value Dv,90 is 500 μm or less; Dv,90 is preferably 400 μm or less; more preferably Dv,90 is 200 μm or less; and still more preferably Dv,90 is 50 μm or less.

In a first method for preparing the EUO zeolite of the invention, the zeolite crystal and crystal aggregate size can be controlled during synthesis and depend on the crystallisation processes as a whole which are controlled by the synthesis parameters. These parameters include supersaturation (reactant concentration), pH (alkalinity), ionic strength (salt addition), solid seed addition, the temperature profile and the mixing and stirring characteristics.

The zeolite with structure type EUO of the invention is obtained, for example, using a synthesis method comprising reacting an aqueous mixture with at least one source of at least one element X selected from silicon and germanium, at least one source of at least one element T selected from aluminium, iron, gallium, boron, titanium, vanadium, zirconium, molybdenum, arsenic, antimony, chromium and manganese, at least one nitrogen-containing organic compound Q selected from alkylated polymethylene α-ω diammonium salt derivatives, an amine degradation product of the derivative, precursors of the derivative, a dibenzyldimethylammonium salt and precursors of that salt. The mixture is reacted until the zeolite crystallises. The alkylated polymethylene α-ω diammonium salt derivative, used in particular for synthesising the EU-1 zeolite, is defined by the formula: $R_1R_2R_3N^+(CH_2)_nN^+R_4R_5R_6$, n being in the range 3 to 14 and $R_1$ to $R_6$ which may be identical or different, representing alkyl or hydroxyalkyl radicals containing 1 to 8 carbon atoms and containing one or more hydroxyl groups, up to five $R_1$ to $R_i$ radicals can be hydrogen.

The reaction mixture is stirred. As an example, the mixture is stirred by applying at least two substantially different stir rates. Preferably, stirring is carried out at a first stir rate then at a second stir rate which is substantially higher than the first stir rate. Thus, for example, the second stir rate is at least 5% higher than the first stir rate, or at least 20% higher than the first stir rate, or at least 50% higher than the first stir rate. The time during which stirring is carried out by applying the first stir rate represents, for example, 90% of the total stirring time or, for example, 95% of the total stirring time.

In a particular implementation, which may or may not be independent of the preceding implementation, seeds S of at least one zeolite which is identical to or different from the EUO zeolite can optionally be used during synthesis. In general, the seed particle size must be calibrated to between 0.005 and 500 μm, preferably in the range 0.01 to 250 μm.

Thus seeds of at least one zeolite, for example with structure type LTA, LTL, FAU, MOR, MAZ, OFF, FER, ERI, BEA, MFI, MTW, MTT, LEV, TON and NES, IM-5 or a NU-85, NU-86, NU-88 zeolite or a zeolite with structure type EUO can be used. Preferably, the seeds used are constituted by seeds of at least one zeolite with structure type LTA, FAU, MOR, MFI or EUO.

In a particular implementation, the seeds are different from the EUO zeolite. They can be different from the EUO zeolite of the invention in their structure type or in the chemical composition of the crystalline framework.

The seeds S are introduced directly after synthesis or after having undergone at least one of the steps selected from the following post synthesis steps, washing, drying, calcining and ion exchange. Seeds can be introduced at any point in the preparation of the EUO zeolite. The seeds can be introduced at the same time as the sources of the metal oxides, or the organic structuring agent, or the seeds can be introduced first into the aqueous mixture, or the seeds can be introduced after introducing the oxide precursors and the structuring agent. Preferably, the seeds are introduced after at least partial homogenisation of the aqueous mixture containing the metal oxide precursors and the structuring agent.

In a further particular implementation, independent or otherwise of the preceding implementation, it may be advantageous to add at least one alkali metal or ammonium salt P to the reaction medium. Examples which can be cited are strong acid radicals such as bromide, chloride, iodide, sulphate, phosphate or nitrate, or weak acid radicals such as organic acid radicals, for example citrate or acetate. This salt can accelerate crystallisation of zeolites with structure type EUO, for example EU-1 zeolite, from the reaction mixture and it can affect the size and form of the crystals of said zeolites.

The mixture used in synthesising the zeolite with structure type EUO generally has the following composition, expressed in the oxide form:

| | |
|---|---|
| $XO_2/T_2O_3$ | at least 10 |
| $OH^-/XO_2$ | 0.002 to 2.0 |
| $Q/XO_2$ | 0.002 to 2.0 |
| $Q/(M^- + Q)$ | 0.1 to 1.0 |
| $H_2O/XO_2$ | 1 to 500 |
| $P/XO_2$ | 0 to 5 |
| $S/XO_2$ | 0 to 0.1 | where

X is silicon and/or germanium,

T is at least one element selected from aluminium, iron, gallium, boron, titanium, vanadium, zirconium, molybdenum, arsenic, antimony, chromium and manganese;

$M^+$ represents an alkali metal or an ammonium ion;

Q represents the organic structuring agent or the decomposition products of said derivative or precursors of the derivative, S represents zeolite seeds expressed in their dried, calcined or exchanged form;

P represents the alkali metal or ammonium salt.

$M^-$ and/or Q can be present in the form of hydroxides or salts of inorganic or organic acids provided that the $OH^-/XO_2$ criterion is satisfied. The preferred alkali metal ($M^-$) is sodium.

The reaction mixture is normally caused to react under autogenous pressure, optionally adding a gas, for example nitrogen, at a temperature in the range 85° C. to 250° C. until zeolite crystals with structure type EUO form, which can take from 1 minute to several months depending on the reactant composition, the mode of heating and the mixture, the working temperature and the degree of stirring.

When the reaction is over, the solid phase is collected on a filter and washed and is then ready for subsequent operations such as drying, calcining and ion exchange.

When the material with structure type EUO being prepared is EU-1 zeolite, the alkylated polymethylene α-ω diammonium derivatives Q are, inter alia, alkylated hexamethylene α-ω diammonium derivatives and especially methylated hexamethylene α-ω diammonium derivatives, more preferably still 1,6-N,N,N,N',N',N',-hexamethylhexamethylenediammonium salts, for example the halide, hydroxide, sulphate, silicate or aluminate. The alkylated polymethylene α-ω diammonium derivatives can be obtained from precursors. Suitable precursors of the starting alkylated polymethylene α-ω diammonium derivatives are in particular the related diamines together with alcohols, alkyl halides, alkanediols or the related alkane halides together with alkylamines, preferably trialkylamines. They can be used as they are in situ or they can be preheated together in the reaction vessel, preferably in solution before adding the other reactants necessary for synthesis of the EU-1 zeolite.

When preparing the ZSM-50 zeolite, the organic structuring agent Q can be a dibenzyldimethylammonium salt such as the halide, hydroxide, sulphate, silicate or aluminate. Dibenzyldimethylammonium salts can be obtained from precursors. Suitable precursors are benzyldimethylamine and a benzyl halide or benzyl alcohol. They can be used as they are in situ or they can be preheated together in the reaction vessel, preferably in solution, before adding the other reactants necessary for synthesis of the ZSM-50 zeolite.

The preferred element X is silicon. The preferred element T is aluminium.

The silicon source can-be any one in normal use envisaged for zeolite synthesis, for example solid powdered silica, silicic acid, colloidal silica or dissolved silica. Powdered silicas which can be used include precipitated silicas, in particular those obtained by precipitation from a solution of an alkali metal silicate such as ZEOSIL or TIXOSIL produced by Rhône-Poulenc, fumed silicas such as aerosils produced by Degussa and "Cabosil" produced by Cabot, and silica gels. Colloidal silicas with a variety of granulometries can be used, such as those sold under trade marks "LUDOX" from Dupont, and "SYTON" from Monsanto. Particular dissolved silicas which can be used are commercially available soluble lasses or silicates containing: 0.5 to 6.0 and in particular 2.0 to 4.0 moles of $SiO_2$ per mole of alkali metal oxide and silicates obtained by dissolving silica in an alkali metal hydroxide, a quaternary ammonium hydroxide or a mixture thereof More advantageously, the aluminium source is sodium aluminate, but it can also be aluminium, an aluminium salt, for example a chloride, nitrate or sulphate, an aluminium alcoholate or alumina itself which should preferably be in a hydrated or hydratable form, such as colloidal alumina, pseudoboehmite, boehmite, gamma alumina or an alpha or beta trihydrate.

Mixtures of the sources cited above can be used. Combined sources of silicon and aluminium can also be used, such as amorphous silica-aluminas or certain clays.

To obtain the hydrogen form of the EUO zeolite of the invention, ion exchange can be carried Out using an acid, in particular a strong mineral acid such as hydrochloric, sulphuric or nitric acid, or with an ammonium compound such as an ammonium salt, for example ammonium chloride, sulphate or nitrate. Ion exchange can be carried out by diluting once or more with the ion exchange solution. The zeolite can be calcined before or after ion exchange, preferably before ion exchange to eliminate all adsorbed organic substances, provided that ion exchange is thereby facilitated.

In a further mode for preparing the zeolite of the invention, independent or otherwise of the preceding preparation modes, the zeolite of the invention is obtained by post-synthesis grinding.

This grinding is carried out on a zeolite with an aggregate Dv,90 of more than 500 $\mu$m. Any grinding technique which is known to the skilled person is suitable. This grinding can be carried out on an as synthesised zeolite, after calcining or after cation exchange, preferably carried out on a calcined and exchanged zeolite, using a dry or wet procedure provided that grinding does not affect the crystallinity of the zeolite.

In a further mode for preparing the zeolite of the invention, which is independent or otherwise of the preceding modes, the crystal aggregate size can be controlled by adjusting the milling conditions before forming.

The invention also concerns a catalyst comprising an EUO zeolite characterized by crystal and crystal aggregate granulometries such that the size of the crystals of EUO zeolite is less than 5 $\mu$m, at least a portion of said zeolite crystals being arranged in the form of aggregates such that the Dv,90 of the aggregates is 500 $\mu$m or less.

The formed catalyst of the present invention contains at least one zeolite with structure type EUO, for example EU-1 zeolite, characterized by a crystal and crystal aggregate granulometry such that the size of the EUO zeolite crystals is less than 5 $\mu$m, preferably less than 0.5 $\mu$m and more preferably less than 0.2 $\mu$m, and the granulometry of the crystal aggregates is such that Dv,90$\leq$500 $\mu$m, preferably Dv,90$\leq$400 $\mu$m, more preferably Dv,90$\leq$200 $\mu$m and still more preferably Dv,90$\leq$50 $\mu$m, at least one metal from group VIII of the periodic table (Handbook of Physics and Chemistry, $76^{th}$ edition), preferably selected from the group constituted by palladium and platinum and still more preferably platinum;

at least one binder, preferably alumina, optionally, at least one element from the group formed by elements from groups IB, IIB, IIIA, IVA, VIB and VIIIB of the periodic table, preferably tin or indium;

optionally, sulphur.

More precisely, the catalyst generally comprises, with respect to the catalyst weight:

1% to 90%, limits included, preferably 3% to 60%, limits included, and more preferably 4% to 40% by weight, limits included, of at least one zeolite with structure type EUO, wherein the granulometry of the crystals and crystal aggregates is as described in the present invention, the zeolite comprising at least one element X selected from germanium and silicon and at least one element T selected from the group formed by aluminium, iron, gallium, boron, titanium, vanadium, zirconium, molybdenum, arsenic, antimony, chromium and manganese, preferably aluminium and boron, with an atomic ratio X/T of 5 or more;

0.01% to 10%, limits included, preferably 0.01% to 2% by weight, limits included, more preferably 0.05% to 1.0%, limits included, of at least one metal from group VIII of the periodic table, preferably selected from the group formed by platinum and palladium and more preferably platinum;

optionally, 0.01% to 10%, limits included, preferably 0.01% to 2%, limits included, and more preferably 0.05% to 1.0% by weight, limits included, of at least one metal from the group formed by groups IB, IIB, IIIA, IVA, VIB and VIIB of the periodic table, preferably selected from the group formed by tin and indium;

optionally, sulphur the quantity of which is such that the ratio of the number of sulphur atoms to the number of deposited group VIII metal atoms is in the range 0.5 to 2, limits included;

the complement to 100% by weight of at least one binder, preferably alumina.

Any forming method is suitable for the present catalyst. As an example, pelletisation or extrusion can be used. The catalyst can also be in the form of beads.

The catalyst of the invention is generally formed such that the catalyst is preferably in the form of extrudates or beads depending on its envisaged use. The conditions for this operation are adjusted so that the size of the EUO zeolite aggregates gives a granulometry of Dv,90≦500 µm.

Any zeolite with structure type EUO which is known to the skilled person and satisfies the granulometry criteria of the present invention is suitable for the catalyst. Thus, for example, the zeolite used as a base to prepare said catalyst can be as synthesised EU-1 zeolite having the required specificities regarding the X/T ratio. The zeolite used can also be ZSM-50 or TPZ-3. Generally, calcining can then be carried out, then at least one ion exchange in at least one $NH_4NO_3$ solution so as to obtain a zeolite with a greater or lesser residual sodium content.

The zeolite with structure type EUO, for example EU-1 zeolite, in the catalyst of the invention is at least partially, preferably practically completely in its acid form, i.e., in the hydrogen form ($H^+$), the sodium content preferably being such that the Na/T atomic ratio is less than 0.5, preferably less than 0.1, more preferably less than 0.02.

The binder (or matrix) in the catalyst prepared using the process of the present invention generally consists of at least one element selected from the group formed by clays, magnesia, aluminas, silicas, titanium oxide, boron oxide, zirconia, aluminium phosphates, titanium phosphates, zirconium phosphates and silica aluminas. Charcoal can also be used. Preferably, the binder is alumina.

The metals can be introduced either all in the same way or using different techniques, at any time in the preparation, before or after forming and in any order. Further, intermediate treatments such as calcining and/or reduction can be carried out between depositions of the different metals.

The catalyst can be prepared using any method known to the skilled person. At least one group VIII element is introduced into the zeolite or onto the binder, preferably onto the binder before or after forming.

One preferred method consists of producing a mixture of the matrix and the zeolite followed by forming. Forming is generally followed by calcining, generally at a temperature in the range 250° C. to 600° C. At least one element from group VIII of the periodic table is introduced after this calcining, preferably by selective deposition onto the binder. Said elements are in practice deposited in an amount of more than 90% in total on the binder and in a manner which is known to the skilled person by controlling the parameters used during said deposition, such as the nature of the precursor used to carry out said deposition.

At least one group VIII element is deposited, preferably onto the zeolite-binder mixture which has already been formed by any process known to the skilled person. Such deposition is, for example, carried out using a dry impregnation step, excess impregnation or ion exchange. Any precursor can be used to deposit these elements. As an example, and preferably, anionic exchange is carried out with hexachloroplatinic acid and/or hexachloropalladic acid in the presence of a competing agent, for example hydrochloric acid. In this case, the metal is in practice deposited in an amount of more than 90% in total onto the binder and it has a good dispersion and good macroscopic distribution through the catalyst grain which constitutes the preferred preparation method.

An example of a method for preparing the catalyst used in the present invention consists of milling the zeolite in a moist gel of matrix (generally obtained by mixing at least one acid and powdered matrix), for example alumina, for a period required to obtain good homogeneity of the paste produced, namely, for example, for about ten minutes, then passing the paste through a die to to form extrudates. Then after oven drying, for example for several hours at about 120° C., and after calcining, for example for two hours at about 500° C., at least one element, for example platinum, is deposited, for example by anion exchange with hexachloroplatinic acid in the presence of a competing agent (for example hydrochloric acid), said deposition being followed by calcining, for example for about 2 hours at about 500° C.

Optionally, at least one element from the group formed by elements from groups IB, IIB, IIIA, IVA, VIB and VIIB is added. Elements from group VIII and groups IB, IIB, IIIA, IVA, VIB and VIIB are added either separately at any stage of the catalyst preparation, or simultaneously in at least one unitary step. When an element from at least one of groups IB, IIB, IIIA, IVA, VIB and VIIB is separately added, then preferably it is added prior to adding the group VIII element. Any depositing technique which is known to the skilled person and any precursor is suitable.

Platinum is generally introduced into the matrix in the form of hexachloroplatinic acid, but ammoniacal compounds or compounds such as ammonium chloroplatinate, dicarbonyl platinum dichloride, hexahydroxyplatinic acid, palladium chloride or palladium nitrate can be used for all noble metals, in this case depositing the noble metal in the zeolite.

Examples which can be cited are platinum II tetramine salts with formula $Pt(NH_3)_4X_2$, platinum IV hexamine salts with formula $Pt(NH_3)_6X_4$, platinum IV halogenopentamine salts with formula $(PtX(NH_3)_5)X_3$; platinum IV tetrahalogenodiamine salts with formula $PtX4(NH_3)_2$ and complexes of platinum with halogen-polyketones and halogenated compounds with formula $H(Pt(acac)_2X)$; X being a halogen selected from the group formed by chlorine, fluorine, bromine and iodine, X preferably being chlorine, and acac representing the group $C_5H_7O_2$ derived from acetylacetone.

The noble metal from the platinum family is preferably introduced by impregnation using an aqueous or organic solution of one of the organometallic compounds cited above. Of the organic solvents which can be used, paraffinic, naphthenic or aromatic hydrocarbons containing 4 to 12 carbon atoms can be cited, and halogenated organic compounds containing, for example, 1 to 12 carbon atoms per molecule. Examples which can be cited are n-heptane, methylcyclohexane, toluene and chloroform. Mixtures of solvents can also be used.

The additional element, optionally introduced in addition, selected from the group formed by elements from groups IB, IIB, IIIA, IVA, VIB and VIIB, can be introduced via compounds such as chlorides, bromides and nitrates or alkyls of elements from groups IB, IIB, IIA, IVA, VIB and VIIB, namely, for example, tin and indium, alkyl tin, indium nitrate and chloride.

This element can also be introduced in the form of at least one organic compound selected from the group formed by complexes of said element, in particular polyketone complexes of metal and hydrocarbylmetals such as metal alkyls, cycloalkyls, aryls and alkylaryls. In the latter case, the metal is advantageously introduced using a solution of an organometallic compound of said metal in an organic solvent. Metal organohalogenated compounds can also be used. Particular metal compounds which can be cited are tetrabutyltin in the case of tin, triphenylindium in the case of indium.

The impregnating solvent is selected from the group formed by paraffinic, naphthenic and aromatic compounds containing 4 to 12 carbon atoms per molecule and halogenated organic compounds containing 1 to 12 carbon atoms per molecule. Examples are n-heptane, methylcyclohexane and chloroform. It is also possible to use mixtures of the solvents defined above.

The additional metal can optionally be introduced at any time during preparation, preferably prior to deposition of one of more of the group VIII metals. If this metal is introduced before the noble metal, the metal compound used is generally selected from the group formed by the metal halide, nitrate, acetate, tartrate, carbonate and oxalate. Introduction is then advantageously carried out in aqueous solution. However, it can also be introduced using a solution of an organometallic compound, for example tetrabutyltin. In this case, before introducing at least one noble metal, calcining is carried out in air.

Preparation of the catalyst generally comprises calcining, normally at a temperature in the rang,e from about 250° C. to 600° C., limits included, for a period of about 0.5 to 10 hours, preferably preceded by drying, for example oven drying, at a temperature in the range from ambient temperature to 250° C., preferably in the range 40° C. to 200° C. Said drying step is preferably carried out during the rise in temperature required to carry out said calcining step.

When the catalyst of the present invention contains sulphur, sulphur is introduced into the formed, calcined catalyst containing the metal or metals cited above, either in situ before the catalytic reaction, or ex-situ. Sulphurisation can optionally be carried out after reduction. With in situ sulphurisation, if the catalyst has not already been reduced, reduction is carried out before sulphurisation. With ex-situ sulphurisation, reduction is carried out followed by sulphurisation. Sulphurisation is carried out in the presence of hydrogen using any sulphurising agent which is known to the skilled person, such as dimethyl sulphide or hydrogen sulphide. As an example, the catalyst is treated with a feed containing dimethyl sulphide in the presence of hydrogen, with a concentration such that the sulphur/metal atomic ratio is 1.5. The catalyst is then kept at about 400° C. for about 3 hours in a stream of hydrogen before injecting the feed.

The catalyst of the present invention is used for isomerising an aromatic C8 cut comprising, for example, either solely a mixture of xylene(s), or solely ethylbenzene, or a mixture of xylene(s) and ethylbenzene. The process is generally carried out under the following operating conditions:

- a temperature in the range 300° C. to 500° C., limits included, preferably in the range 320° C. to 450° C., limits included, and more preferably in the range 340° C. to 430° C., limits included;
- a partial pressure of hydrogen in the range 0.3 to 1.5 MPa, limits included, preferably in the range 0.4 to 1.2 MPa, limits included, more preferably in the range 0.6 to 1.2 MPa, limits included;
- a total pressure in the range 0.45 to 1.9 MPa, limits included, preferably in the range 0.6 to 1.5 MPa, limits included;
- a space velocity, expressed as kilograms of feed introduced per kilogram of catalyst per hour, in the range 0.25 to 30 $h^{-1}$, limits included, preferably in the range 1 to 25 $h^{-1}$, limits included, and more preferably in the range 2 to 15 $h^{-1}$, limits included.

The invention will now be illustrated by the following examples.

EXAMPLES 1 AND 2

Comparative

EU-1 zeolites with different Si/Al ratios and with crystal aggregate granulometries not in accordance with the invention, and catalysts containing these zeolites.

As synthesised EU-1 zeolites Z1 and Z2 comprising the organic structuring agent, silicon and aluminium, had an overall Si/Al atomic ratio of 14.2 and 36.1 respectively, crystal sizes in the range 20 to 30 nm and in the range 30 to 50 nm and a sodium content of about 0.85% and 0.5% with respect to the weight of dry EU-1 zeolite.

The EU-1 zeolites first underwent dry calcining at 550° C. in a stream of air (1 l/g/h) for 6 hours. The solids obtained underwent three ion exchange steps in a 10 N $NH_4NO_3$ solution at about 100° C. for 4 hours for each exchange and with a volume ratio of solution to the mass of dry zeolite of 10 $cm^3/g$.

At the end of these treatments, the EU-1 zeolites Z1' and Z2' in the $NH_4$ form had an overall Si/Al atomic ratio of 15.6 and 36.1 respectively and a sodium content of 55 ppm and 80 ppm by weight with respect to the weight of dry EU-1 zeolite.

For the zeolite Z1', a laser granulometry measurement resulted in a Dv,90 of 905 4m before ultrasound, and after a cumulative 15.5 min of ultrasound, the Dv,90 was 580 $\mu$m.

For the zeolite Z2', the Dv,90 was 715 $\mu$m before ultrasound and after a cumulative 15.5 min of ultrasound, the Dv,90 was 565 $\mu$m.

The EU-1 zeolites were then formed by extrusion with an alumina gel to obtain, after drying and calcining in dry air, supports S1 and S2 constituted by 1.4 mm diameter extrudates containing 10% by weight of EU-1 zeolite in the H form and 90% of alumina.

The supports S1 and S2 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalysts A and B produced contained, by weight, 10.0% of EU-1 zeolite in its hydrogen form, 89.7% of alumina and 0.3% of platinum.

EXAMPLES 3 AND 4

In Accordance with the Invention

EU-1 zeolites with different Si/Al ratios with a granulometry in accordance with the invention, obtained by grinding Z1' and Z2' zeolites and the corresponding catalysts.

The EU-1 zeolites Z1' and Z2' described in the preceding example were used. Before extrusion, a dry grinding step was inserted leading to zeolites Z3 and Z4. The X ray diffraction diagrams showed that the decree of crystallinity of the zeolites had not been modified during the grinding step and REM microscopy revealed that the crystals had not been altered (size in the range 20–50 nm).

Laser granulometry measurements for Z3 gave a Dv,90 of 56.4 $\mu$m before ultrasound, and a Dv,90 of 45.9 $\mu$m after 3.5 minutes of ultrasound; and in the case of Z4 to a Dv,90 of 11.0 $\mu$m before ultrasound, and a Dv,90 of 10.6 $\mu$m after 0.5 minutes of ultrasound.

These EU-1 zeolites then underwent forming by extrusion as described in the preceding example.

Supports S3 and S4 obtained were used to prepare catalysts C and D using the same methods as those used in the case of catalysts A and B.

Catalysts C and D obtained contained, by weight, 10.0% of EU-1 zeolite in its hydrogen form, 89.7% of alumina and 0.3% of platinum.

EXAMPLES 5 AND 6

In Accordance with the Invention

EU-1 zeolites with different Si/Al ratios with crystal aggregate granulometries in accordance with the invention obtained during synthesis, and the corresponding catalysts.

A solution 1 composed of silicon and structuring agent was prepared by diluting hexamethonium bromide (Fluka, 97%) in 80% of the water required to form a gel then adding a colloidal silica sol (Ludox HS40, Dupont, 40% $SiO_2$). Solid sodium hydroxide (Prolabo, 99%) and solid sodium aluminate (Prolabo, 46% $Al_2O_3$, 33% $Na_2O$) were then dissolved in 10% of the water required for gel formation, to form a solution 2. Solution 2 was added to solution 1 with stirring, then the remaining water (10%). Mixing was carried out until the medium was homogeneous. The resulting mixture was reacted in a 1000 ml autoclave with stirring at 300 rpm for 120 hours then with stirring at 450 rpm for 5 hours (Example 5) and with stirring at 300 rpm for 92 hours then with stirring at 450 rpm for 4 hours (Example 6) at 180° C. under autogenous pressure. After cooling, the product was filtered and washed with 3.5 litres of demineralised water then dried in a ventilated oven at 120° C. The molar compositions of the synthesis mixtures and the quantities of reactants introduced are recorded in Tables 1 and 2:

TABLE 1

| Examples | 5 (Si/Al = 15) | 6 (Si/Al = 40) |
|---|---|---|
| $SiO_2$ (mol) | 420 | 420 |
| $Al_2O_3$ (mol) | 14 | 5.25 |
| $Na_2O$ (mol) | 70 | 52.5 |
| $HxBr_2$ (mol) | 140 | 140 |
| $H_2O$ (mol) | 19600 | 19600 |

$HxBr_2$ = hexamethonium bromide = $Me_3N(CH_2)_6NMe_3^{2+}(Br^-)_2$

TABLE 2

| Examples | 5 (Si/Al = 15) | 6 (Si/Al = 40) |
|---|---|---|
| Colloidal silica (g) | 101.5 | 102.0 |
| Sodium aluminate (g) | 5.0 | 1.9 |
| Sodium hydroxide (g) | 6.9 | 6.0 |
| $HxBr_2$ (g) | 84.2 | 84.5 |
| Water (g) | 502.4 | 505.6 |

$HxBr_2$ = hexamethonium bromide = $Me_3N(CH_2)_6NMe_3^{2+}(Br^-)_2$

The results of X ray diffraction and chemical analyses show that under these conditions, zeolites Z5 and Z6 (pure EU-1 and with a maximum yield) were obtained.

These as synthesised EU-1 zeolites Z5 and Z6 comprising the organic structuring agent, silicon and aluminium, had an overall Si/Al atomic ratio of 13.8 and 37.2 respectively, crystal sizes in the range 20 to 100 nm and in the range 30 to 50 nm and a sodium content of about 1.0% and 0.3% with respect to the weight of dry EU-1 zeolite.

Laser granulometry measurements for the EU-1 zeolite with a Si/Al ratio of 13.8 gave a Dv,90 of 16.8 μm before ultrasound and to a Dv,90 of 16.8 μm after a cumulative 0.5 minutes of ultrasound; and in the case of the EU-1 zeolite with a Si/Al ratio of 37.2, to a Dv,90 of 25.6 μm before ultrasound, and to a Dv,90 of 25.5 μm after a cumulative 0.5 minutes of ultrasound.

The EU-1 zeolites Z5 and Z6 first underwent dry calcining at 550° C. in a stream of air (1 l/g/h) for 6 hours. The solids obtained underwent three ion exchange steps in a 10 N $NH_4NO_3$ solution at about 100° C. for 4 hours for each exchange and with a ratio of the volume of solution to the mass of dry zeolite of 10 $cm^3/g$.

At the end of these treatments, the EU-1 zeolites Z5' and Z6' in the $NH_4$ form had an overall Si/Al atomic ratio of 14.8 and 37.3 respectively and a sodium content of 49 ppm and 65 ppm by weight with respect to the weight of dry EU-1 zeolite.

For the zeolite Z5', a laser granulometry measurement resulted in a Dv,90 of 16.3 4m before ultrasound and after a cumulative 0.5 min of ultrasound, the Dv,90 was 16.1 μm; for the zeolite Z6', the Dv,90 was 25.2 μm before ultrasound and after a cumulative 0.5 min of ultrasound, the Dv,90 was 25.1 μm.

These zeolites were then formed in the same proportions and using the method described above to obtain supports S5 and S6.

Catalysts E and F produced from supports 5S and S6 using the methods described for Examples 1 and 2 contained, by weight, 10.0% of EU-1 zeolite in its hydrogen form, 89.7% of alumina and 0.3% of platinum.

EXAMPLES 7 TO 11

In Accordance with the Invention

EU-1 zeolites with different Si/Al ratios with crystal aggregate granulometries in accordance with the invention obtained during synthesis in the presence of seeds (7 and 8), structuring agent precursors (9) or seeds and structuring agent precursors (10 and 11).

A solution 1 composed of silicon and structuring agent was prepared by diluting hexamethonium bromide (Fluka, 97%) or the two precursors (dibromohexane and trimethylamine) in 80% of the water required to form a gel then adding a colloidal silica sol (Ludox HS40, Dupont, 40% $SiO_2$). Solid sodium hydroxide (Prolabo, 99%) and solid sodium aluminate (Prolabo, 46% $Al_2O_3$, 33% $Na_2O$) were then dissolved in 10% of the water required for gel formation, to form a solution 2. Solution 2 was added to solution 1 with stirring, then the remaining water (10%). Mixing was carried out until the medium was homogeneous and the EU-1 seeds, if used, were introduced at this stage. The resulting mixture was reacted in a 125 ml autoclave at 180° C. under autogenous pressure, with stirring. After cooling, the product was filtered and washed with 0.5 litres of demineralised water then dried in a ventilated oven at 120° C. The molar compositions of the synthesis mixtures and the quantities of reactants introduced are recorded in Tables 3 and 4:

TABLE 3

| Examples | 7 Si/Al = 15 | 8 Si/Al = 40 | 9 Si/Al = 15 | 10 Si/Al = 15 | 11 Si/Al = 40 |
|---|---|---|---|---|---|
| $SiO_2$ (mol) | 60 | 60 | 60 | 60 | 60 |
| $Al_2O_3$ (mol) | 2 | 0.75 | 2 | 2 | 0.75 |
| $Na_2O$ (mol) | 10 | 10 | 10 | 10 | 10 |
| $HxBr_2$ (mol) | 20 | 20 | 0 | 0 | 0 |
| DBH (mol) | 0 | 0 | 20 | 20 | 20 |
| TMA (mol) | 0 | 0 | 40 | 40 | 40 |
| $H_2O$ (mol) | 2800 | 2800 | 2800 | 2800 | 2800 |
| EU-1/$SiO_2$ (g/g) | 0.04 | 0.04 | 0 | 0.04 | 0.04 |

$HxBr_2$ = hexamethonium bromide = $Me_3N(CH_2)_6NMe_3^{2+}(Br^-)_2$
DBH = dibromomethane
TMA = trimethylamine

TABLE 4

| Examples | 7 Si/Al = 15 | 8 Si/Al = 40 | 9 Si/Al = 15 | 10 Si/Al = 15 | 11 Si/Al = 40 |
|---|---|---|---|---|---|
| Colloidal silica (g) | 14.50 | 14.53 | 14.50 | 14.50 | 14.53 |
| Sodium aluminate (g) | 0.72 | 0.27 | 0.72 | 0.72 | 0.27 |

TABLE 4-continued

| Examples | 7 Si/Al = 15 | 8 Si/Al = 40 | 9 Si/Al = 15 | 10 Si/Al = 15 | 11 Si/Al = 40 |
|---|---|---|---|---|---|
| Sodium hydroxide (g) | 0.99 | 1.18 | 0.99 | 0.99 | 1.18 |
| HxBr$_2$ (g) | 12.03 | 12.05 | 0 | 0 | 0 |
| DBH (g) | 0 | 0 | 8.02 | 8.02 | 8.04 |
| TMA (g) | 0 | 0 | 8.45 | 8.45 | 8.47 |
| Water (g) | 71.77 | 71.97 | 67.33 | 67.33 | 67.52 |
| EU-1 seeds (g) | 0.23 | 0.23 | 0 | 0.23 | 0.23 |

HxBr$_2$ = hexamethonium bromide = Me$_3$N(CH$_2$)$_6$NMe$_3$$^{2+}$(Br$^-$)$_2$
DBH = dibromomethane
TMA = trimethylamine The synthesis times used are shown in Table 5 (pure EU-1 and with a maximum yield). The chemical analyses and the laser diffraction results obtained are also shown in Table 5.

TABLE 5

| Examples | 7 Si/Al = 15 | 8 Si/Al = 40 | 9 Si/Al = 15 | 10 Si/Al = 15 | 11 Si/Al = 40 |
|---|---|---|---|---|---|
| Time (h) | 96 | 72 | 110 | 85 | 65 |
| Si/Al (XRD) | 13.4 | 36.9 | 14.4 | 14.2 | 34.6 |
| Dv, 90 no US | 18.0 | 28.1 | 21.2 | 32.2 | 25.3 |
| Dv, 90 with US | 17.3 | 22.5 | 19.4 | 26.8 | 22.8 |

US: ultrasound

US: Ultrasound

Further, REM microscopy showed that the size of the EU-1 zeolite crystals obtained was in the range 20 to 100 nm.

An analysis of the results shows that the different synthesis methods, with seeds, with structuring agent precursors or with seeds and structuring agent precursors all led to solids with the granulometry criteria of the invention.

EXAMPLE 12

Comparing Catalytic Performances of Comparative Examples and Catalysts of the Invention by Isomerising an Aromatic C8 Cut The catalytic performances of the six catalysts A to F were evaluated by isomerising an aromatic C8 cut principally containing meta-xylene, ortho-xylene and ethylbenzene. The tests were carried out on 5 g of catalyst with no hydrogen recycle. The operating conditions were as follows:

temperature: 390° C.

total pressure: 15 bar, (1 bar=0.1 MPa);

hydrogen partial pressure: 12 bar.

The catalysts were first treated with a feed containing dimethyl disulphide (DMDS) in the presence of hydrogen, with a concentration such that the sulphur/metal atomic ratio was 1.5. The catalyst was then kept at 400° C. for 3 hours in a stream of hydrogen then the feed was injected.

The catalysts were compared in terms of their activity (by approximate equilibria of paraxylene and ethylbenzene, and by ethylbenzene conversion) and their selectivity by net losses at iso-approximate equilibrium of para-xylene.

Side reactions lead to three types of losses: losses to paraffins essentially resulting from naphthene ring opening reactions followed by cracking; losses to aromatics formed by dismutation and transalkylation of aromatic compounds containing 8 carbon atoms (AC8) and finally, losses to naphthalenes, namely naphthenes containing 8 carbon atoms (N8) due to hydrogenation of aromatic compounds. N8 can be recycled, so the net losses corresponding to the sum of the losses by cracking and dismutation/transalkylation including naphthenes other than N8 are compared.

In order to calculate the approximate equilibrium (AEQ), the concentrations of para-xylenes (%pX) are expressed with respect to the three xylene isomers.

The approximate equilibrium (AEQ) is defined as follows:

$$pXAEQ\ (\%)=100\times(\%pX_{effluent}-\%pX_{feed})/(\%pX_{equilibrium}-\%pX_{feed})$$

The cracking losses (P1) are the AC8 losses in the form of C1 to C8 paraffins (PAR):

$$P1(wt\ \%)=100\times[(\%PAR_{effluent}\times weight\ of\ effluent)-(\%PAR_{feed}\times weight\ of\ feed)]/(\%AC8_{feed}\times weight\ of\ feed)$$

The dismutation/transalkylation losses (P2) are the AC8 losses in the form of naphthenes other than N8, toluene, benzene and C9+aromatics (OAN):

$$P2(wt\ \%)=100\times[(\%OAN_{effluent}\times weight\ of\ effluent)-(\%OAN_{feed}\times weight\ of\ feed)]/(\%AC8_{feed}\times weight\ of\ feed)$$

The sum of losses P1 and P2 represents the net losses.

The data shown in Table 6 were obtained under iso-experimental conditions to compare the catalysts as regards activity.

TABLE 6

| Catalysts | A (comp) | B (comp) | C | D | E | F |
|---|---|---|---|---|---|---|
| pX AEQ (%) | 98.4 | 95.9 | 98.5 | 96.3 | 98.3 | 96.5 |
| EB conversion (%) | 56.2 | 46.5 | 59.1 | 48.4 | 59.4 | 48.6 |

It can be seen from the results shown in Table 6 that the catalysts with the required granulometry (C, D, E and F) had a substantially improved activity as regards ethylbenzene conversion with respect to prior art catalysts (A and B) for an equivalent Si/Al ratio. The method of obtaining the required granulometry had no influence on the catalytic result since catalysts C and D (using grinding) and E and F (adapted synthesis method) were equivalent at the same Si/Al ratio.

These catalysts were also compared in terms of selectivity at iso pX AEQ by varying the mass flow rate of the feed. These results are shown in Table 7.

TABLE 7

| Catalyst | A (comp) | B (comp) | C | D | E | F |
|---|---|---|---|---|---|---|
| pX AEQ (%) | 95.6 | 95.3 | 95.7 | 95.5 | 95.3 | 95.2 |
| EB conversion (%) | 49.2 | 45.6 | 52.0 | 47.8 | 51.8 | 47.7 |
| Net losses (wt %) | 4.9 | 5.4 | 5.0 | 5.5 | 4.8 | 5.3 |

At an iso pX AEQ and for identical Si/Al, it can be seen from the results of Table 7 that the granulometry does not affect the selectivity since the net losses are identical.

The catalysts prepared in accordance with the present invention are thus more active than prior art catalysts, particularly as regards ethylbenzene conversion, and are as selective as prior art catalysts.

In general, the lower limit for the Dv,90 value of the granulometry of the aggregates, is 40 nanometers (nm).

Consequently, a Dv,90 value of 500 microns (μm) or less means, as explained above, that the diameter of 90% of the equivalent spheres of the aggregates have a diameter of 500 μm to not less than 40 nm.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 98/16.421, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A zeolite with structure type EUO comprising EUO zeolite crystals with a size of less than 5 μm, at least a portion of the EUO zeolite crystals being in the form of EUO zeolite aggregates, characterized in that the granulometry of said aggregates is such that the value of Dv,90 is in the range of 200 μm to 40 nm.

2. A zeolite according to claim 1, in which the value of the Dv,90 of the aggregates is 50 μm or less.

3. A zeolite according to claim 2, in which the size of the zeolite crystals is less than 0.2 μm.

4. A zeolite according to claim 1, in which the size of the zeolite crystals is less than 0.5 μm.

5. A zeolite according to claim 1, in which the size of the zeolite crystals is less than 0.2 μm.

6. A zeolite according to claim 1, comprising at least one element X selected from silicon and germanium and at least one element T selected from the group formed by aluminium, iron, gallium, boron, titanium, vanadium, zirconium, molybdenum, arsenic, antimony, chromium and manganese, the overall atomic ratio X/T being 5 or more.

7. A zeolite according to claim 6, in which the element X is silicon and the element T is aluminium.

8. A zeolite according to claim 1, in which the zeolite is EU-1 zeolite.

9. A process for preparing a zeolite according to claim 1, comprising reacting an aqueous mixture with at least one source of at least one element X, at least one source of at least one element T, at least one organic nitrogen-containing compound Q selected from alkylated derivatives of an α-ω diammonium polymethylene salt, an amine degradation product of the derivative, precursors of the derivative, a dibenzyldimethylammonium salt and precursors of said salt.

10. A process according to claim 9, in which the reaction mixture is stirred by applying at least two substantially different stir rates.

11. A process according to claim 10, in which stirring is carried out at a first stir rate then at a second stir rate which is substantially higher than the first stir rate.

12. A process according to claim 9, in which seeds S of at least one zeolite are added to the reaction mixture.

13. A process according to claim 12, in which the zeolite seeds are introduced after homogenising at least part of the aqueous mixture containing the source of element X, the source of element T, and the source of the organic structuring agent.

14. A process for preparing a catalyst according to claim 13, comprising mixing said EUO zeolite and a binder, forming the mixture, introducing at least one group VIII metal and conducting at least one calcining step.

15. A preparation process according to claim 14, comprising introducing at least one element selected from the group formed by elements from groups IB, IIB, IIIA, IVA, VIB and VIIB of the periodic table.

16. A process according to claim 9, in which the organic nitrogen-containing compound Q is selected from alkylated polymethylene α-ω diammonium salt derivatives defined by the formula: $R_1R_2R_3N^+(CH_2)_nN^+R_4R_5R_6$, n being in the range 3 to 14 and $R_1$ to $R_6$, which may be identical or different, representing alkyl or hydroxyalkyl radicals containing 1 to 8 carbon atoms; up to five $R_1$ to $R_6$ radicals can be hydrogen.

17. A process according to claim 9, in which at least one alkali metal or ammonium salt P is added.

18. A process according to any one of claims 9 to 13, 16 and 17 which the aqueous mixture has the following composition:

| | |
|---|---|
| $XO_2/T_2O_3$ | at least 10 |
| $OH^-/XO_2$ | 0.002 to 2.0 |
| $Q/XO_2$ | 0.002 to 2.0 |
| $Q/(M^- + Q)$ | 0.1 to 1.0 |
| $H_2O/XO_2$ | 1 to 500 |
| $P/XO_2$ | 0 to 5 |
| $S/XO_2$ | 0 to 0.1. |

19. A zeolite produced in accordance with the process of claim 9.

20. A zeolite produced in accordance with the process of claim 13.

21. A zeolite produced in accordance with the process of claim 16.

22. A zeolite produced in accordance with the process of claim 17.

23. A zeolite produced in accordance with the process of claim 18.

24. A process for preparing a zeolite according to claim 1, in which an as synthesised zeolite with an aggregate Dv,90 of more than 500 μm is ground.

25. A catalyst comprising an EUO zeolite according to claim 1, and at least one catalytically active metal from at least one of groups IB, IIB, IIIA, IVA, VIB, VIIB and VIII of the periodic table.

26. A catalyst comprising a zeolite of structure type EUO in accordance with claim 1.

27. A catalyst according to claim 26, comprising at least one binder and at least one metal from group VIII of the periodic table.

28. In a process for catalytically isomerising aromatic compounds containing 8 carbon atoms per molecule at a temperature in the range 300° C. to 500° C. limits included, at a hydrogen partial pressure in the range 0.3 to 1.5 MPa limits included, at a total pressure in the range 0.45 to 1.9 MPa limits included, with a space velocity, expressed in kilograms of feed introduced per kilogram of catalyst per hour, in the range 0.25 to 3 h$^{-1}$ limits included, the improvement wherein the catalyst is in accordance with claim 27.

29. A catalyst according to claim 27, comprising at least one metal selected from the group formed by elements from groups IB, IIB, IIIA, IVA, a VIB and VIIB of the periodic table.

30. In a process for catalytically isomerising aromatic compounds containing 8 carbon atoms per molecule at a temperature in the range 300° C. to 500° C. limits included, at a hydrogen partial pressure in the range 0.3 to 1.5 MPa limits included, at a total pressure in the range 0.45 to 1.9 MPa limits included, with a space velocity, expressed in kilograms of feed introduced per kilogram of catalyst per hour, in the range 0.25 to 30 $h^{-1}$ limits included, the improvement wherein the catalyst is in accordance with claim 29.

31. A catalyst according to claim 27, in which the zeolite is at least partially in the acid form.

32. A catalyst according to claim 27, comprising sulphur.

33. A catalyst according to claim 26, in which the zeolite is at least partially in the acid form.

34. In a process for catalytically isomerising aromatic compounds containing 8 carbon atoms per molecule at a temperature in the range 300° C. to 500° C. limits included, at a hydrogen partial pressure in the range 0.3 to 1.5 MPa limits included, at a total pressure in the range 0.45 to 1.9 MPa limits included, with a space velocity, expressed in kilograms of feed introduced per kilogram of catalyst per hour, in the range 0.25 to 30 $h^{-1}$ limits included, the improvement wherein the catalyst is in accordance with claim 33.

35. A catalyst according to claim 26, comprising sulphur.

36. In a process for catalytically isomerising aromatic compounds containing 8 carbon atoms per molecule at a temperature in the range 300° C. to 500° C. limits included, at a hydrogen partial pressure in the range 0.3 to 1.5 MPa limits included, at a total pressure in the range 0.45 to 1.9 MPa limits included, with a space velocity, expressed in kilograms of feed introduced per kilogram of catalyst per hour, in the range 0.25 to 30 $h^{-1}$ limits included, the improvement wherein the catalyst is in accordance with claim 35.

37. In a process for catalytically isomerising aromatic compounds containing 8 carbon atoms per molecule at a temperature in the range 300° C. to 500° C. limits included, at a hydrogen partial pressure in the range 0.3 to 1.5 MPa limits included, at a total pressure in the range 0.45 to 1.9 MPa limits included, with a space velocity, expressed in kilograms of feed introduced per kilogram of catalyst per hour, in the range 0.25 to 30 $h^{-1}$ limits included, the improvement wherein the catalyst is in accordance with claim 26.

38. A zeolite with structure type EUO comprising EUO zeolite crystals with a size of less than 5 µm, at least a portion of the EUO zeolite crystals being in the form of EUO zeolite aggregates, characterized in that the granulometry of said aggregates is such that the value of Dv,90 is in the range of 400 µm to 40 nm.

39. A process for producing a zeolite according to claim 38, comprising reacting an aqueous mixture with at least one source of at least one element X, at least one source of at least one element T, at least one organic nitrogen-containing compound Q selected from alkylated derivatives of an α-ω diammonium polymethylene salt, an amine degradation product of the derivative, precursors of the derivative, a dibenzyldimethylammonium salt and precursors of said salt.

40. A process according to claim 39, in which the reaction mixture is stirred by applying at least two substantially different stir rates.

41. A process according to claim 40, in which stirring is carried out at a first stir rate then at a second stir rate which is substantially higher than the first stir rate.

42. A process according to claim 39, in which seeds S of at least one zeolite are added to the reaction mixture.

43. A process according to claim 42, in which the zeolite seeds are introduced after homogenizing at least part of the aqueous mixture containing the source of element X, the source of element T, and the source of the organic structuring agent.

44. A process according to claim 39, in which the organic nitrogen-containing compound Q is selected from alkylated polymethylene a-w diammonium salt derivatives defined by the formula: $R_1R_2R_3N^+(CH_2)_nN^+R_4R_5R_6$, n being in the range 3 to 14 and $R_1$ to $R_6$, which may be identical or different, representing alkyl or hydroxyalkyl radicals containing 1 to 8 carbon atoms; up to five $R_1$ to $R_6$ radicals can be hydrogen.

45. A process according to claim 39, in which at least one alkali metal or ammonium salt P is added.

46. A process according to claim 39, in which the aqueous mixture has the following composition:

| | |
|---|---|
| $XO_2/T_2O_3$ | at least 10 |
| $OH^-/XO_2$ | 0.002 to 2.0 |
| $Q/XO_2$ | 0.002 to 2.0 |
| $Q/(M^+ + Q)$ | 0.1 to 1.0 |
| $H_2O/XO_2$ | 1 to 500 |
| $P/XO_2$ | 0 to 5 |
| $S/XO_2$ | 0 to 0.1. |

47. A catalyst comprising an EUO zeolite in accordance with claim 38.

48. A catalyst according to claim 46, comprising at least one binder and at least one metal from group VIII of the periodic table.

49. In a process for catalytically isomerising aromatic compounds containing 8 carbon atoms per molecule at a temperature in the range 300° C. to 500° C. limits included, at a hydrogen partial pressure in the range 0.3 to 1.5 MPa limits included, at a total pressure in the range 0.45 to 1.9 MPa limits included, with a space velocity, expressed in kilograms of feed introduced per kilogram of catalyst per hour, in the range 0.25 to 30 $h^{-1}$ limits included, the improvement wherein the catalyst is in accordance with claim 48.

50. A catalyst according to claim 46, in which the zeolite is at least partially in the acid form.

51. A catalyst according to claim 46, comprising at least one metal selected from the group formed by elements from groups IB, IIB, IIIA, IVA, VIB and VIB of the periodic table.

52. A catalyst according to claim 46, comprising sulphur.

53. In a process for catalytically isomerising aromatic compounds containing 8 carbon atoms per molecule at a temperature in the range 300° C. to 500° C. limits included, at a hydrogen partial pressure in the range 0.3 to 1.5 MPa limits included, at a total pressure in the range 0.45 to 1.9 MPa limits included, with a space velocity, expressed in kilograms of feed introduced per kilogram of catalyst per hour, in the range 0.25 to 30 $h^{-1}$ limits included, the improvement wherein the catalyst is in accordance with claim 52.

54. A process for preparing a catalyst according to claim 47, comprising mixing said EUO zeolite and a binder, forming the mixture; introducing at least one group VIII metal and conducting at least one calcining step.

55. In a process for catalytically isomerising aromatic compounds containing 8 carbon atoms per molecule at a temperature in the range 300° C. to 500° C. limits included, at a hydrogen partial pressure in the range 0.3 to 1.5 MPa limits included, at a total pressure in the range 0.45 to 1.9 MPa limits included, with a space velocity, expressed in kilograms of feed introduced per kilogram of catalyst per hour, in the range 0.25 to 30 $h^{-1}$ limits included, the improvement wherein the catalyst is in accordance with claim 47.

56. A catalyst comprising an EUO zeolite according to claim 38, and at least one catalytically active metal from at least one of groups IB, IIB, IIIA, IVA, VIB, VIIB and VIII of the periodic table.

57. In a process for catalytically isomerising aromatic compounds containing 8 carbon atoms per molecule at a temperature in the range 300° C. to 500° C. limits included, at a hydrogen partial pressure in the range 0.3 to 1.5 MPa limits included, at a total pressure in the range 0.45 to 1.9 MPa limits included, with a space velocity, expressed in kilograms of feed introduced per kilogram of catalyst per hour, in the range 0.25 to 30 $h^{-1}$ limits included, the improvement wherein the catalyst is in accordance with claim 56.

58. A zeolite according to claim 38, in which the size of the zeolite crystals is less than 0.2 $\mu$m.

* * * * *

UNITED STATES PATENT AND TRADEMARK OFFICE
CERTIFICATE OF CORRECTION

PATENT NO. : 6,514,479 B1
DATED : February 4, 2003
INVENTOR(S) : Elisabeth Merlen et al.

It is certified that error appears in the above-identified patent and that said Letters Patent is hereby corrected as shown below:

<u>Column 16,</u>
Line 16, reads "to any one claims 9 to 13, 16 and 17" should read -- to claim 9, in --
Line 58, reads "0.25 to 3" should read -- 0.25 to 30 --
Line 63, reads "IVA, a VIB" should read -- IVA, IVB --

<u>Column 18,</u>
Lines 24, 37, 39 and 42, reads "according to claim 46," should read -- according to claim 47, --
Line 41, reads "VIB and VIB" should read -- VIB and VIIB --

Signed and Sealed this

Twenty-third Day of March, 2004

JON W. DUDAS
*Acting Director of the United States Patent and Trademark Office*